(12) United States Patent
Tchirikov

(10) Patent No.: US 9,072,755 B2
(45) Date of Patent: Jul. 7, 2015

(54) HYPOTONIC AQUEOUS COMPOSITION WITH REDUCED CHLORIDE CONTENT, WITH OR WITHOUT PHOSPHOLIPIDS

(76) Inventor: Michael Tchirikov, Halle (DE)

(*) Notice: Subject to any disclaimer, the term of this patent is extended or adjusted under 35 U.S.C. 154(b) by 0 days.

(21) Appl. No.: 13/978,052

(22) PCT Filed: Jan. 4, 2012

(86) PCT No.: PCT/EP2012/000029
§ 371 (c)(1),
(2), (4) Date: Jul. 2, 2013

(87) PCT Pub. No.: WO2012/093087
PCT Pub. Date: Jul. 12, 2012

(65) Prior Publication Data
US 2013/0316980 A1 Nov. 28, 2013

(30) Foreign Application Priority Data
Jan. 5, 2011 (EP) .................................... 11000044

(51) Int. Cl.
| A61K 31/685 | (2006.01) |
| A01N 57/26 | (2006.01) |
| A61K 31/661 | (2006.01) |
| A61K 31/688 | (2006.01) |
| A61K 33/14 | (2006.01) |

(52) U.S. Cl.
CPC ............. A61K 31/661 (2013.01); A61K 31/685 (2013.01); A61K 31/688 (2013.01); A61K 33/14 (2013.01)

(58) Field of Classification Search
CPC ... A61K 31/66; A61K 31/685; A61K 31/688; A61K 33/14
USPC ......................................... 514/75, 76, 77, 78
See application file for complete search history.

(56) References Cited

U.S. PATENT DOCUMENTS

2008/0038372 A1* 2/2008 Kabayama et al. ........... 424/663

FOREIGN PATENT DOCUMENTS

| EP | 0998916 A1 | 5/2000 |
| EP | 1719517 A1 | 11/2006 |

OTHER PUBLICATIONS

International Search Report for PCT/EP2012/000029 dated Jun. 20, 2012.
Brace et al Article: Amniotic Fluid Volume Responses to Amnio-Infusion of Amniotic Fluid Versus Lactated Ringer's Solution in Fetal Sheep. J Soc Gynecol Investig vol. 11, No. 6 Sep. 1, 2004 pp. 363-368.
Corpening James W et al Article: Ingested bovine amniotic fluid enhances morphine antinociception in rats. Physiology & Behavior vol. 70, No. 1-2, Jul. 2000 pp. 15-18.
Dio Shigeharu et al Article: Effect of Maternal Hydration on Oligohydramnios: A Comparison of Three Volume Expansion Methods. Obstetrics and Gynecology, vol. 92, No. 4 Part 1, Oct. 1998, pp. 525-529.
Tchirikov Michael et al Article: Long-term amnioinfusion through a subcutaneously implanted amniotic fluid replacement port system for treatment of PPROM in humans. European Journal of Obstetrics & Gynecology and Reproductive Biology, Sep. 2010, vol. 152, No. 1, pp. 30-33.
Ringer's Solution Wikipedia Retrieved from the Internet dated May 12, 2008.
Almong et al., "A Methodology for Determination of Phospholipids," *Analytical Biochemistry*, 188:237-242 (1990).
Chaiworapongsa et al., "Amniotic Fluid Concentration of Surfactant Proteins in Intra-Amniotic Infection," *J. Matern Fetal Neonatal Med.*, 21(9):663-670 (2008).
Chaiworapongsa et al., "The Concentration of Surfactant Protein-A in Amniotic Fluid Decreases in Spontaneous Human Parturition at Term," *The Journal of Maternal-Fluid and Neonatal Medicine*, 21(9):652-659 (2008).
De Santis et al., "Transabdominal Amnioinfusion Treatment of Severe Oligohydramnios in Preterm Premature Rupture of Membranes at Less than 26 Gestational Weeks," *Fetal Diagn. Ther.*, 18:412-417 (2003).
Gesteland et al., "Intramembranous Solute and Water Fluxes During High Intramembranous Absorption Rates in Fetal Sheep with and without Lung Liquid Diversion," *American Journal of Obstetrics & Gynecology*, 201:85.e1-85.e6 (2009).
Goldenberg et al., "Epidemiology and Causes of Preterm Birth," *The Lancet*, 371:75-84 (2008).
Gratacos et al., "Current Experience with Fetoscopy and the Eurofoetus Registry for Fetoscopic Procedures," *European Journal of Obstetrics & Gynecology and Reproductive Biology*, 92:151-159 (2000).
Hsu et al., "The Experience of Amnioinfusion for Oligohydramnios During the Early Second Trimester," *Taiwan J Obstet Gynecol.*, 46(4):395-398 (2007).

(Continued)

*Primary Examiner* — My-Chau T Tran
(74) *Attorney, Agent, or Firm* — Marshall, Gerstein & Borun LLP

(57) ABSTRACT

An aqueous composition for application in a method for surgical or therapeutic treatment of the human or animal body or in a diagnostic procedure which is practiced on the human or animal body, the composition comprising osmotically active particles and containing less than 70 μl$^{-1}$ of amniotic cells, the osmolarity of the composition being in the range from 240.0 mosm/l to less than 308.0 mosm/l, and the chloride ion concentration in the composition being not more than 130.0 mmol/l. An aqueous composition for application with an amniotic infusion, the composition containing less than 70 μl$^{-1}$ of amniotic cells and comprising at least one surfactant, is also disclosed.

39 Claims, No Drawings

(56) References Cited

OTHER PUBLICATIONS

Lohninger et al., "Relationships Among Human Amniotic Fluid Dipalmitoyl Lecithin, Postpartum Respiratory Compliance, and Neonatal Respiratory Distress Syndrome," *Clin. Chem.*, 29(4):650-655 (1983).

Ogunyemi et al., "A Case Controlled Study of Serial Transabdominal Amnioinfusions in the Management of Second Trimester Oligohydramnios Due to Premature Rupture of Membranes," *European Journal of Obstetrics & Gynecology and Reproductive Biology*, 102:167-172 (2002).

Ross et al., "Amniotic Fluid Ionic Concentration in Response to Chronic Fetal Vasopressin Infusion," *Perinatal Research Laboratories*, pp. E287-E291 (1985).

Simhan et al., "Preterm Premature Rupture of Membranes: Diagnosis, Evaluation and Management Strategies," *BJOG: An International Journal of Obstetrics and Gynaecology*, 112(Supp. 1):32-37 (2005).

Tan et al., "Test Amnioinfusion to Determine Suitability for Serial Therapeutic Amnioinfusion in Midtrimester Premature Rupture of Membranes," *Fetal Diagn. Ther.*, 18:183-189 (2003).

Tranquilli et al., "Transabdominal Amnioinfusion in Preterm Premature Rupture of Membranes: A Randomised Controlled Trial," *BJOG: An International Journal of Obstetrics and Gynaecology*, 112:759-763 (2005).

van Kamp et al., "Complications of Intrauterine Intravascular Transfusion for Fetal Anemia Due to Maternal Red-Cell Alloimmunization," *American Journal of Obstetrics & Gynecology*, 192:171-177 (2005).

\* cited by examiner

HYPOTONIC AQUEOUS COMPOSITION WITH REDUCED CHLORIDE CONTENT, WITH OR WITHOUT PHOSPHOLIPIDS

BACKGROUND OF THE INVENTION

1. Field of the Invention

The present invention relates to a hypotonic aqueous composition with reduced chloride content and with or without phospholipids for application in a method for the surgical or therapeutic treatment of the human or animal body or in a diagnostic method performed on the human or animal body. Particular emphasis is given to the use of the aqueous composition for application in a method for the therapeutic treatment of the human body, especially as amniotic fluid replacement, more particularly in amnioinfusion, preferably in the case of preterm premature rupture of membranes.

2. Related Technology

Preterm premature rupture of membranes (PPROM) is one of the main causes of perinatal morbidity and mortality. It occurs in 3% of all pregnancies and is responsible for a third of all premature births (Mercer B M. Preterm premature rupture of the membranes. Obstet Gynecol 2003; 101: 178-193). Important risk factors for PPROM are infections (Goldenberg R L, Culhane J F, Iams J D, Romero R. Epidemiology and causes of preterm birth. Lancet 2008; 371: 75-84), polyhydramnios (Simhan H N, Canavan T P. Preterm premature rupture of membranes: diagnosis, evaluation and management strategies. BJOG 2005; 112: 32-37), invasive prenatal diagnostics (Van Kamp I L, Klumper F J, Oepkes D, et al. Complications of intrauterine intravascular transfusion for fetal anemia due to material red-cell alloimmunization. Am J Obstet Gynecol 2005: 192: 171-177) and fetoscopic procedures (Gratacos E, Deprest J. Current experience with fetoscopy and the Eurofoetus Registry for fetoscopic procedures. Eur J Obstet Gynecol Reprod Biol 2000; 92: 151-159). In the event of occurrence of pulmonary hypoplasia, the perinatal mortality risk is about 80%.

The goal of therapeutic measures for the treatment of PPROM is to restore and to maintain the normal fluid volume in the amniotic cavity. To increase the amniotic fluid index (AFI), the fluid volume in the amniotic cavity is continuously increased by amnioinfusion (Tan L K et al. Test amnioinfusion to determine suitability for serial therapeutic amnioinfusion in midtrimester premature rupture of membranes. Fetal Diagn Ther 2003; 18: 183-189; Tranquillli A L et al. Transabdominal amnioinfusion in preterm premature rupture of membranes: a randomized controlled trial. BJOG 2005; 112: 759-763; Hsu T L et al. The experience of amnioinfusion for oligohydramnios during the early second trimester. Taiwan J Obstet Gynecol 2007; 46 (4)).

To replenish the fluid volume in the amniotic cavity, an isotonic salt solution is usually used in order to avoid any damage to the fetus as far as possible. Tested isotonic salt solutions include a physiological saline solution (0.9% by weight NaCl; osmolarity: 308 mosm/l), a Ringer's solution, a Ringer's lactate solution and a Ringer's acetate solution.

The Ringer's infusion solution contains:
8.60 g/l (147 mmol/l) NaCl
0.30 g/l (4.0 mmol/l) KCl and
0.33 g/l (2.2 mmol/l) $CaCl_2$.

The Ringer's lactate solution contains:
5.9 g/l-6.1 g/l (125 mmol/l-134 mmol/l) NaCl
0.3 g/l-0.4 g/l (4.0 mmol/l-5.4 mmol/l) KCl
0.22 g/l-0.29 g/l (0.9 mmol/l-2.0 mmol/l) $CaCl_2*2H_2O$ and
2.8 g/l-3.45 g/l (25 mmol/l-31 mmol/l) $CH_3CHOHCOONa$.

Its theoretical osmolarity is between 262 mosm/l and 293 mosm/l.

The Ringer's acetate solution contains:
6.00 g/l (130 mmol/l) NaCl
0.40 g/l (5.4 mmol/l) KCl
0.134 g/l (0.9 mmol/l) $CaCl_2*2H_2O$
0.203 g/l (1.0 mmol/l) $MgCl_2*6H_2O$
3.70 g/l (27 mmol/l) $CH_3COONa*3H_2O$
Its theoretical osmolarity is 276 mosm/l.

The physiological saline solution has been found to be the most effective.

However, the currently known methods for amnioinfusion for treating PPROM are not satisfactory, since the fluid filled from the outside (isotonic salt solution) drains away again from the uterus very rapidly, thereby greatly reducing the effect of amnioinfusion. The known methods involved, for example, cervical occlusion with a fibrin gel (Zamlynski J, Bodzek P, Olejek A, Grettka K, Manka G. Results of amnioinfusion in pregnancies with oligohydramnios and non-ruptured fetal membranes. Med Wieku Rozwoj 2003; 7: 187-194) or the infusion of a fluid via a transcervical catheter (Machalski T, Sikora J, Bakon I, Magnucki J, Grzesiak-Kubica E, Szkodny E. Short-term and long-term fetal heart rate variability after amnioinfusion treatment of oligohydramnios complicated pregnancy. Ginekol Pol 2001; 72: 1107-1111).

Even repeated transabdominal amnioinfusions with physiological saline solution for the treatment of PPROM showed only minimal advantages in a treatment within 6 h after fluid loss (De Santis M, Scavo M, Noia G, Masini L, Piersigilli F, Romagnoli C, Caruso A. Transabdominal amnioinfusion treatment of severe oligohydramnios in preterm premature rupture of membranes at less than 26 gestational weeks. Fetal Diagn Ther 2003; 18: 412-417; Ogunyemi D, Thompson W. A case controlled study of serial transabdominal amnioinfusions in the management of second trimester oligohydramnios due to premature rupture of membranes. Eur J Obstet Gynecol Reprod Biol. 2002; 102: 167-172).

Against this background, long-term amnioinfusion of physiological saline solution by means of a subcutaneously implanted amniotic fluid replacement port system for the treatment of PPROM in humans has been proposed. This approach enabled pregnancy to be extended by several weeks while avoiding pulmonary hypoplasia (Tchirikov M, Steetskamp J, Hohmann M, Koelbl H. Long-term amnioinfusion through a subcutaneously implanted amniotic fluid replacement port system for treatment of PPROM in humans. Eur J Obstet Gynecol Reprod Biol. 2010; 152: 30-33).

Studies concerning the composition of amniotic fluid have also already been published. It is assumed that the phospholipids present in human amniotic fluid are responsible for fetal lung maturation (Lohninger A, Salzer H, Simbruner G, Husslein P, Martin G. Relationship among human amniotic fluid dipalmitoyl lecithin, postpartum respiratory compliance and neonatal respiratory distress syndrome. Clin. Chem. 1983; 29: 650-655; Almog R, Anderson-Samsonoff C, Berns D S, Saulsbery R. A methodology for determination of phospholipids. Analytical Biochemistry 1990; 188: 237-242). Corresponding preparations based on phospholipids from bovine lung have been available on the market for some time for the treatment of premature babies suffering from respiratory distress syndrome (ALVEOFACT®, SURVANTA®).

ALVEOFACT® contains, per 1.2 ml, 50.76 mg-60 mg of phospholipid fraction from bovine lung (surfactant; corresponds to 50 mg of total phospholipids) and also sodium chloride and sodium hydrogencarbonate (Rote Liste 2000).

SURVANTA® contains, per 8 ml, 72.8 mg-211.2 mg of phospholipid fraction from bovine lung, 18.4 mg-157.6 mg of 1,2-dipalmitoyl-sn-glycero-3-phosphocholine, 1.4 mg-11.1 mg of palmitic acid, 2.2 mg-10.5 mg of glyceryl tripalmitate (corresponds to 50 mg of total phospholipids) and also sodium chloride and sodium hydrogencarbonate or hydrochloric acid (Rote Liste 2000).

It has been further found that the concentration of surfactant proteins changes in the event of intraamniotic infections (Chaiworapongsa T, Hong J S, Hull W M, Romero R, Whitsett J A. Amniotic fluid concentration of surfactant proteins in intra-amniotic infection. J Matern Fetal Neonatal Med. 2008; 21: 663-670) and falls in the case of spontaneous childbirth on the expected date of birth (Chaiworapongsa T, Hong J S, Hull W M, Kim C J, Gomez R, Mazor M, Romero R, Whitsett J A. The concentration of surfactant protein-A in amniotic fluid decreases in spontaneous human parturition at term. J Matern Fetal Neonatal Med. 2008; 21: 652-659).

Furthermore, our studies have revealed that the osmolarity, i.e., the number of osmotically active particles per liter of solution, in human amniotic fluid is lower than in physiological saline solution (308 mosm/l). In addition, the chloride ion concentration in amniotic fluid is also distinctly lower than in physiological saline solution.

Against this background, it has to be assumed that amnioinfusion, more particularly long-term amnioinfusion, with a physiological saline solution, as currently favored according to the prior art, is disadvantageous for a fetus for several reasons:

Firstly, the administration of an infusion solution having an excessively high osmolarity increases the osmolarity of the amniotic fluid, which is continually drunk and excreted by the fetus. Particularly in the case of long-term administration of the infusion solution, this can cause damage to the organs of the fetus, especially its skin, its eyes and its digestive organs, more particularly its kidneys. In addition, there is reason to fear a change in the fetal programming which might lead to hypertension in later life, even if this has so far not yet been described owing to lack of relevant data.

A similar argument applies to the administration of an infusion solution having an excessively high chloride ion concentration. It increases the chloride ion concentration of the amniotic fluid, which is continually drunk and excreted by the fetus. Particularly in the case of long-term administration of the infusion solution, this can cause damage to the organs of the fetus, especially its skin, its eyes and its digestive organs, more particularly its kidneys. In addition, there is reason to fear a change in the fetal programming which might lead to problems in later life, even if this has so far not yet been described owing to lack of relevant data.

Furthermore, the administration of an infusion solution which does not contain any phospholipids lowers the concentration of the phospholipids in the amniotic fluid, which is in continuous contact with the alveoli of the fetus. Particularly in the case of long-term administration of the infusion solution, this can lead to rinsing out of the phospholipids on the alveoli of the fetus and thus to slowing of lung maturation in the fetus. As a result, the chances of survival for such a fetus are distinctly reduced.

In addition, the administration of an infusion solution which does not contain any surfactant proteins lowers the concentration of the surfactant proteins in the amniotic fluid. Particularly in the case of long-term administration of the infusion solution, this can lead to damage to the organs of the fetus.

From the prior art, fetoscopic procedures are also known in which the amnion is opened, the amniotic fluid is at least partly removed, the fetus is operated on, the amnion is reclosed, and the removed amniotic fluid is at least partly returned to the amniotic cavity.

For medical and ethical reasons, it is not possible to use the amniotic fluid removed in this manner for the treatment of PPROM in other patients. Firstly, the fetus that has been operated on requires the amniotic fluid after the operation in order to increase its chances of survival. Furthermore, the removed amniotic fluid contains tissue remnants and considerable amounts of DNA from the fetus that has been operated on (J Cln Endocrinol Metab 2000; 85: 214-8 "Large amounts of cell-free fetal DNA are present in amniotic fluid"). Amniotic fluid can, for example, contain 778 fetal cells and more in 1 mm$^3$. These tissue remnants and this large amount of DNA can lead to unwanted reactions to the genetically foreign material and/or to infections in another fetus or its mother.

For similar reasons, it is, without hesitation, also not possible to use animal amniotic fluid for the treatment of PPROM in humans. Firstly, owing to the tissue remnants and large amounts of DNA of the animal fetus that are present in this amniotic fluid, there is reason to fear unwanted reactions of the fetus and/or of the mother to the genetically foreign material and/or infections. In addition, there is the possible risk of formation of chimeras as a result of mixing of genetic information, which is prohibited in most countries by law.

The publication by Brace R A et al., Amniotic fluid volume responses to amnio-infusion of amniotic fluid versus lactated Ringer's solution in fetal sheep. J Soc Gynecol Investig. 2004, 11(6): 363-368, describes amnioinfusion of amniotic fluid in pregnant sheep, the amniotic fluid used having previously been obtained from other sheep fetuses.

However, when using amniotic fluid from sheep in amnioinfusion in another mammal, more particularly in humans, there is a considerable risk of hereditary material from the animal, for example the DNA of the sheep, being incorporated into the DNA of the fetus and so-called chimeras being formed. Therefore, it is not meaningful to use animal amniotic fluid in amnioinfusion in another mammal, more particularly in humans, especially since the production of chimeras is prosecutable in most countries.

Furthermore, it would not be meaningful to use amniotic fluid from sheep for long-term amnioinfusions due to PPROM in other mammals, more particularly in humans, who are the focus of the present invention. For instance, a human fetus drinks between 200 ml and 700 ml of amniotic fluid every day and the skin and also the mucous membranes of the fetus are partially permeable for the surrounding amniotic fluid. In the case of PPROM, it is necessary to infuse about 2 liters of amniotic fluid every day over several months. If it should be seriously contemplated that this large amount of amniotic fluid be obtained from animals for these purposes, there is the risk, in some cases, of infections being transmitted directly from the animals to the fetus and also to the expectant mother. There is reason to fear this, especially for infections which cannot be completely avoided by means of sterilization of the animal amniotic fluid, for example prion transmission.

Apart from that, the sodium ion concentration (121.4 mmol/L) and the calcium ion concentration (0.75 mmol/L) in ovine amniotic fluid are significantly lower than in human amniotic fluid (Gesteland K M et al. Intramembranous solute and water fluxes during high intramembranous absorption rates in fetal sheep with and without lung liquid diversion. American Journal of Obstetrics & Gynecology, 2009 85.e1-85.e6; Ross M G et al. Amniotic fluid ionic concentration in response to chronic fetal vasopressin infusion. American Physiological Society 1985 E287-E291).

The publication by Corpening J W et al., Ingested bovine amniotic fluid enhances morphine antinociception in rats.

Physiology & Behavior 2000 (70) 15-18, concerns the administration of bovine amniotic fluid to rats.

However, when using bovine amniotic fluid in amnioinfusion in other mammals, for example rats, there is a considerable risk of bovine hereditary material being incorporated into the DNA of the fetus and so-called chimeras being formed. Therefore, it is not meaningful to use bovine amniotic fluid in amnioinfusion in other mammals, more particularly in humans, especially since the production of chimeras is prosecutable in most countries.

The publication by Doi S et al., Effect of Maternal Hydration on Oligohydramnios: A Comparison of Three Volume Expansion Methods. Obstetrics & Gynecology 1998, 92 (4), 525-529, studies the influence of intravenous administration of an isotonic fluid or of a hypotonic fluid and also of an oral administration of water on the amniotic fluid index (AFI) in women. The hypotonic solution used is Ringer's solution. It has an excessively high chloride ion concentration with the associated disadvantages (see above).

The patent application EP 1 719 517 A1 relates to an artificial physiological saline solution having an osmolarity in the range from 260 mOsm/l to 320 mOsm/l, which preferably contains not more than 200 mmol/l chloride ions. However, the chloride ion concentration is much higher than required here. Concerning the disadvantages of an excessively high chloride ion concentration, reference is made to the above explanations.

The patent application EP 0 998 916 A1 is concerned with medical compositions for administration across the mucous membrane. The compositions are said to have an osmolarity lower than 290 mOsm/l. However, the only example with an osmolarity in the range required here has an excessively high chloride ion concentration. Concerning the disadvantages of an excessively high chloride ion concentration, reference is again made to the above explanations.

SUMMARY OF THE INVENTION

In view of the prior art, it is therefore an object of the present invention to demonstrate better options for treating patients suffering from preterm premature rupture of membranes (PPROM). A solution to the disadvantages and problems of the current amnioinfusion methods is desired in particular. For instance, it shall be demonstrated in particular how health risks for the fetus, more particularly the risk of premature birth, can be avoided as far as possible. In addition, very rapid and very effective lung maturation is desired in order to increase the chances of survival of the fetus, even in the event of a premature birth. Furthermore, damage to organs of the fetus, especially its skin, its eyes and its digestive organs, more particularly its kidneys, shall be avoided as far as possible. It is also important in this connection to avoid a change in the fetal programming of the fetus as far as possible. Lastly, the solution according to the invention shall also be realized cost-effectively in a comparably simple manner and be inoffensive from a moral, ethical and legal standpoint.

In a first aspect, the invention provides an aqueous composition for application in a method for the surgical or therapeutic treatment of the human or animal body or in a diagnostic method performed on the human or animal body, wherein the composition comprises osmotically active particles and contains fewer than 70 amniotic cells per µl, wherein the osmolarity of the composition is in the range from 240.0 mosm/l to less than 308.0 mosm/l and the chloride ion concentration in the composition is not more than 130.0 mmol/l.

In a second aspect, the invention provides an aqueous composition for application in amnioinfusion, wherein the composition contains fewer than 70 amniotic cells per µl and the composition contains at least one surfactant.

DETAILED DESCRIPTION

Both providing an aqueous composition which is as yet unknown for medical applications and which comprises osmotically active particles and contains fewer than 70 amniotic cells per µl, wherein the osmolarity of the composition is in the range from 240.0 mosm/l to less than 308.0 mosm/l and wherein the chloride ion concentration in the composition is not more than 130.0 mmol/l, and providing an aqueous composition which is as yet unknown for application in amnioinfusion and which contains fewer than 70 amniotic cells per µl and at least one surfactant allows better treatment of patients suffering from preterm premature rupture of membranes (PPROM).

Particularly the disadvantages and problems of the current amnioinfusion methods are overcome as a result. For instance, options are demonstrated with respect to how health risks for the fetus, more particularly the risk of premature birth, can be avoided as far as possible. In addition, particularly in the version according to the second aspect of the invention, comparatively rapid and effective lung maturation is ensured, which in turn distinctly increases the chances of survival of the fetus, even in the event of a premature birth. Furthermore, particularly in the version according to the first aspect of the invention, damage to organs of the fetus, especially its skin, its eyes and its digestive organs, more particularly its kidneys, is ideally avoided. The risk of a change in the fetal programming of the fetus is ideally reduced particularly in the version according to the first aspect of the invention. Lastly, the solution according to the invention can also be realized cost-effectively in a comparably simple manner and is completely inoffensive from a moral, ethical and legal standpoint.

In a first aspect, the present invention relates to an aqueous composition for application in a method for the surgical or therapeutic treatment of the human or animal body or in a diagnostic method performed on the human or animal body. Particular emphasis is given to methods for therapeutic treatment, particularly of the human body. A particularly preferred application area is amnioinfusion, especially long-term amnioinfusion, preferably in humans, more particularly for the treatment of patients suffering from preterm premature rupture of membranes (PPROM), especially of expectant mothers in the second trimester (week 13 to week 24) and third trimester (week 25 to week 40), more particularly in weeks 16 to 34.

In addition, it is advantageous to use said composition according to the invention for all medical applications in which a preferably hypotonic aqueous composition is used. Particularly preferred application areas include the rinsing of body cavities, preferably the rinsing out of purulent cavities, more particularly in the lungs, for example in the context of bronchoalveolar lavage, and also the rinsing of body regions covered with membranes, more particularly mucous membranes. In this case, it is particularly advantageous to apply the composition according to the invention especially for the treatment of babies and toddlers under 3 years of age, preferably under 2 years of age, more preferably under 1 year of age, even more preferably under 6 months of age, especially under 3 months of age.

The osmolarity of said composition according to the invention is less than that of physiological saline solution and thus less than 308.0 mosm/l. Preferably, it is less than 307.0 mosm/l, more preferably less than 305.0 mosm/l, even more preferably less than 303.0 mosm/l, yet even more preferably not more than 300.0 mosm/l, yet still even more preferably not more than 290.0 mosm/l, especially not more than 280.0 mosm/l.

In addition, the osmolarity of said composition according to the invention is at least 240.0 mosm/l, preferably at least 250.0 mosm/l, especially at least 260.0 mosm/l, in order to avoid lysis of cells as far as possible.

Particularly preferably, the osmolarity of said composition according to the invention is in the range from 240.0 mosm/l to 300.0 mosm/l, more preferably in the range from 250.0 mosm/l to 290.0 mosm/l, especially in the range from 260.0 mosm/l to 280.0 mosm/l.

The chloride ion concentration in said composition according to the invention is not more than 130.0 mmol/l and thus less than that in physiological saline solution and in the aforementioned Ringer's solutions. Preferably, it is less than 130.0 mmol/l, more preferably less than 125.0 mmol/l, especially not more than 120.0 mmol/l.

In addition, the chloride ion concentration in said composition according to the invention is preferably at least 90.0 mmol/l, more preferably at least 100.0 mmol/l, especially at least 105.0 mmol/l.

Particularly preferably, the chloride ion concentration in said composition according to the invention is in the range from 100.0 mmol/l to 120.0 mmol/l, especially in the range from 105.0 mmol/l to 115.0 mmol/l.

The sodium ion concentration in said composition according to the invention is preferably less than that in physiological saline solution and thus preferably less than 154.0 mmol/l. More preferably, it is less than 150.0 mmol/l, especially not more than 145.0 mmol/l. However, it is preferably greater than 125.0 mmol/l, more preferably at least 130.0 mmol/l, and is preferably in the range from 130.0 mmol/l to 145.0 mmol/l, especially in the range from 130.0 mmol/l to 140.0 mmol/l.

The potassium ion concentration in said composition according to the invention is preferably in the range from 3.5 mmol/l to 5.2 mmol/l, especially in the range from 3.5 mmol/l to 4.5 mmol/l.

The calcium ion concentration in said composition according to the invention is preferably less than 8.0 mmol/l, more preferably less than 6.0 mmol/l, even more preferably less than 4.0 mmol/l, and is preferably in the range from 1.0 mmol/l to 3.0 mmol, more preferably in the range from 1.0 mmol/l to 2.5 mmol/l, especially in the range from 1.5 mmol/l to less than 2.3 mmol/l.

The magnesium ion concentration in said composition according to the invention is preferably in the range from 0.0 mmol/l to 2.0 mmol/l, more preferably in the range from 0.1 mmol/l to 1.5 mmol/l, even more preferably in the range from 0.1 mmol/l to 1.0 mmol/l, especially in the range from 0.1 mmol/l to less than 0.8 mmol/l.

The urea concentration in said composition according to the invention is preferably in the range from 0.0 mg/dl to 10.0 mg/dl.

The uric acid concentration in said composition according to the invention is preferably in the range from 0.0 mg/dl to 5.0 mg/dl.

The phosphate ion concentration in said composition according to the invention is preferably in the range from 0.0 mg/dl to 8.0 mg/dl, especially in the range from 0.1 mg/dl to 7.0 mg/dl.

The glucose concentration in said composition according to the invention is preferably in the range from 0.0 mg/dl to 340.0 mg/dl. It is more preferably less than 300.0 mg/dl, even more preferably less than 200.0 mg/dl, yet even more preferably less than 100.0 mg/dl, especially less than 60.0 mg/dl. In a very particularly preferred embodiment of the present invention, the composition contains less than 50.0 mg/dl, preferably less than 25.0 mg/dl, more preferably less than 10.0 mg/dl, especially zero, glucose.

The concentration of the lactate salts in said composition according to the invention is preferably in the range from 0.0 mmol/l to 20.0 mmol/l.

The concentration of the citrate salts in said composition according to the invention is preferably in the range from 0.0 mg/l to 100.0 mg/l.

The hydrogencarbonate ion concentration in said composition according to the invention is preferably in the range from 5.0 mmol/l to 100.0 mmol/l, more preferably in the range from 5.0 mmol/l to 50.0 mmol/l, even more preferably in the range from 5.0 mmol/l to less than 24.0 mmol/l, especially in the range from 10.0 mmol/l to 20.0 mmol/l.

The total protein concentration in said composition according to the invention is preferably in the range from 0.0 g/l to 10.0 g/l.

The albumin concentration in said composition according to the invention is preferably in the range from 0.0 g/dl to 5.0 g/dl, especially in the range from 0.0 g/dl to less than 2.0 g/dl.

The copper ion concentration in said composition according to the invention is preferably in the range from 0.0 µg/dl to 150.0 µg/dl, more preferably in the range from 1.0 µg/dl to 100.0 µg/dl, especially in the range from 5.0 µg/dl to 50.0 µg/dl.

The selenium ion concentration in said composition according to the invention is preferably in the range from 0.0 µg/dl to 50.0 µg/dl, more preferably in the range from 1.0 µg/dl to 25.0 µg/dl, especially in the range from 2.0 µg/dl to 15.0 µg/dl.

The zinc ion concentration in said composition according to the invention is preferably in the range from 0.0 µg/dl to 30.0 µg/dl, more preferably in the range from 5.0 µg/dl to 25.0 µg/dl, especially in the range from 10.0 µg/dl to 24.0 µg/dl.

In the present invention, it was found that it is particularly advantageous to add at least one surfactant to the aqueous compositions according to the invention, more particularly for lung maturation of the fetus in amnioinfusion.

Accordingly, protection is sought in the present invention for an aqueous composition for application in amnioinfusion that contains fewer than 70 amniotic cells per µl and at least one surfactant, more particularly at least one phospholipid and/or at least one surfactant protein. With regard to the preferred application areas of said composition, to the preferred components of said composition, to the preferred concentrations of said components and to the osmolarity, what has been said above and will be said below applies in principle, with the exception of the stated osmolarity and the stated chloride ion concentration not necessarily having to be fulfilled under these circumstances.

The composition according to the first aspect of the invention likewise advantageously contains at least one surfactant.

In the present invention, the term "surfactant" refers to surface-active substances which are to be found in human lungs. They are normally formed by specialized pulmonary cells (type II pneumocytes) and include in particular phospholipids and surfactant proteins.

In a first particularly preferred embodiment of the present invention, the composition according to the first aspect of the invention contains at least one phospholipid. In a second particularly preferred embodiment of the present invention, the composition according to the first aspect of the invention contains at least one surfactant protein. In a further particularly preferred embodiment of the present invention, the composition according to the first aspect of the invention contains at least one phospholipid and at least one surfactant protein.

Phospholipids (phosphatides) which are particularly preferred according to the invention include lipoidal triglycerides containing two long-chain fatty acids and a phosphoric acid moiety to which preferably a base is additionally bonded. Very particular preference is given to those compounds which occur in animal and plant cells, especially in the brain, in the heart, in the liver, in egg yolk and in soybeans.

Phospholipids which are very particularly advantageous for the purposes of the present invention include O-phosphatidylethanolamine and O-phosphatidylcholine. The stereochemistry of these compounds is not subject to any particular restrictions. However, it is particularly favorable to use the 1-sn-phosphatidylethanolamine and the 3-sn-phosphatidylcholine, more particularly the 2,3-diacyl-sn-glycero-1-phosphoethanolamine (previously known as cephalin) and the 1,2-diacyl-sn-glycero-3-phosphocholine (previously known as lecithin). The use of O-phosphatidylcholine, preferably 3-sn-phosphatidylcholine, especially 1,2-diacyl-sn-glycero-3-phosphocholine has been found to be very particularly advantageous, with particular preference being given to dipalmitoylphosphatidylcholine.

Sphingolipids are a further class of phospholipids which are particularly preferred according to the invention. These include in particular compounds in which the glycerol has been replaced by an unsaturated amino alcohol, preferably sphingosine. Sphingosine phosphates are usually also referred to as sphingomyelin.

In a particularly preferred version of the present invention, the compositions according to the invention contain a mixture of phosphatides which, in addition to the at least one phospholipid, contains one or more saturated or unsaturated fatty acids, particularly preferably palmitic acid, stearic acid, oleic acid, linoleic acid and/or linolenic acid.

In the compositions according to the invention, the weight ratio of phospholipid to surfactant protein is preferably in the range from 5:1 to 15:1, more preferably in the range from 8:1 to 12:1, especially in the range from 9:1 to 11:1.

Surfactant proteins which are particularly preferred for the purposes of the present invention comprise biophysical surfactant proteins, more particularly surfactant protein B and surfactant protein C, immunological surfactant proteins, more particularly surfactant protein A and surfactant protein D, and regulatory surfactant proteins.

The total lipid concentration in the compositions according to the invention is preferably in the range from 0.0 mg/l to 2000.0 mg/l, more preferably in the range from 1.0 mg/l to 1500.0 mg/l, even more preferably in the range from 25.0 mg/l to 1000.0 mg/l, especially in the range from 50.0 mg/l to 500.0 mg/l.

The phosphatidylcholine concentration in the compositions according to the invention is preferably in the range from 0.0 mg/l to 1000.0 mg/l, more preferably in the range from 1.0 mg/l to 500.0 mg/l, even more preferably in the range from 10.0 mg/l to 250.0 mg/l, especially in the range from 50.0 mg/l to 150.0 mg/l. The weight fraction of phosphatidylcholine, based on all lipids, is preferably greater than 50.0% by weight, more preferably greater than 70.0% by weight and is very particularly preferably in the range from 75.0% by weight to 85.0% by weight.

The dipalmitoylphosphatidylcholine concentration in the compositions according to the invention is preferably in the range from 0.0 mg/l to 600.0 mg/l, more preferably in the range from 1.0 mg/l to 400.0 mg/l, even more preferably in the range from 10.0 mg/l to 250.0 mg/l, especially in the range from 20.0 mg/l to 150.0 mg/l. The weight fraction of dipalmitoylphosphatidylcholine, based on phosphatidylcholine, is preferably in the range from 36.0% by weight to 60.0% by weight.

The palmitoylmyristolphosphatidylcholine concentration in the compositions according to the invention is preferably in the range from 0.0 mg/l to 200.0 mg/l, more preferably in the range from 1.0 mg/l to 100.0 mg/l, even more preferably in the range from 2.0 mg/l to 50.0 mg/l, especially in the range from 2.5 mg/l to 10.0 mg/l.

The phosphatidylglycerol concentration in the compositions according to the invention is preferably in the range from 0.0 mg/l to 200.0 mg/l, more preferably in the range from 1.0 mg/l to 100.0 mg/l, even more preferably in the range from 2.0 mg/l to 50.0 mg/l, especially in the range from 5.0 mg/l to 20.0 mg/l. The weight fraction of phosphatidylglycerol, based on phosphatidylcholine, is preferably in the range from 5.0% by weight to 20.0% by weight, especially in the range from 10.0% by weight to 15.0% by weight.

The phosphatidylethanolamine concentration in the compositions according to the invention is preferably in the range from 0.0 mg/l to 100.0 mg/l, more preferably in the range from 1.0 mg/l to 50.0 mg/l, even more preferably in the range from 2.0 mg/l to 25.0 mg/l, especially in the range from 3.0 mg/l to 10.0 mg/l. The weight fraction of phosphatidylethanolamine, based on phosphatidylcholine, is preferably in the range from 1.0% by weight to 10.0% by weight, especially in the range from 3.0% by weight to 7.0% by weight.

The phosphatidylinositol concentration in the compositions according to the invention is preferably in the range from 0.0 mg/l to 70.0 mg/l, more preferably in the range from 1.0 mg/l to 50.0 mg/l, even more preferably in the range from 1.5 mg/l to 25.0 mg/l, especially in the range from 2.0 mg/l to 10.0 mg/l. The weight fraction of phosphatidylinositol, based on phosphatidylcholine, is preferably in the range from 1.0% by weight to 10.0% by weight, especially in the range from 2.0% by weight to 6.0% by weight.

The phosphatidylserine concentration in the compositions according to the invention is preferably in the range from 0.0 mg/l to 50.0 mg/l, more preferably in the range from 0.1 mg/l to 25.0 mg/l, even more preferably in the range from 0.2 mg/l to 10.0 mg/l, especially in the range from 0.5 mg/l to 5.0 mg/l. The weight fraction of phosphatidylserine, based on phosphatidylcholine, is preferably in the range from 0.1% by weight to 10.0% by weight, especially in the range from 0.5% by weight to 2.5% by weight.

The sphingomyelin concentration in the compositions according to the invention is preferably in the range from 0.0 mg/l to 1000.0 mg/l, more preferably in the range from 1.0 mg/l to 500.0 mg/l, even more preferably in the range from 5.0 mg/l to 100.0 mg/l, especially in the range from 10.0 mg/l to 40.0 mg/l. Advantageously, it is adapted to the age of the fetus, analogous to natural amniotic fluid, with a lower concentration being selected for younger fetuses and a higher concentration for older fetuses.

The lysophospholipid concentration in the compositions according to the invention is preferably in the range from 0.0 mg/l to 10.0 mg/l, more preferably in the range from 0.1 mg/l to 5.0 mg/l, even more preferably in the range from 0.2 mg/l to 2.5 mg/l, especially in the range from 0.3 mg/l to 1.0 mg/l. The weight fraction of lysophospholipid, based on phosphatidylcholine, is preferably in the range from 0.1% by weight to 5.0% by weight and is more preferably less than 1.0% by weight.

The weight ratio of lecithin to sphingomyelin in the compositions according to the invention is preferably greater than 1.5; more preferably greater than 1.75; especially greater than 2.0.

The cholesterol concentration in the compositions according to the invention is preferably in the range from 0.0 mg/l to 100.0 mg/l, more preferably in the range from 1.0 mg/l to 50.0 mg/l, even more preferably in the range from 2.0 mg/l to 25.0 mg/l, especially in the range from 3.0 mg/l to 10.0 mg/l. The weight fraction of cholesterol, based on all lipids, is preferably in the range from 1.0% by weight to 20.0% by weight, especially in the range from 5.0% by weight to 10.0% by weight.

The concentration of surfactant protein A in the compositions according to the invention is preferably in the range from 0.0 mg/l to 500.0 mg/l, more preferably in the range from 1.0 mg/l to 100.0 mg/l, even more preferably in the range from 2.0 mg/l to 50.0 mg/l, especially in the range from 3.0 mg/l to 10.0 mg/l.

The concentration of surfactant protein B in the compositions according to the invention is preferably in the range from 0.0 mg/l to 100.0 mg/l, more preferably in the range from 0.1 mg/l to 50.0 mg/l, even more preferably in the range from 0.2 mg/l to 10.0 mg/l, especially in the range from 0.3 mg/l to 2.0 mg/l.

The concentration of surfactant protein D in the compositions according to the invention is preferably in the range from 0.0 μg/l to 1000.0 μg/l, more preferably in the range from 1.0 mg/l to 500.0 mg/l, even more preferably in the range from 2.0 mg/l to 100.0 mg/l, especially in the range from 3.0 mg/l to 25.0 mg/l.

The pH of the compositions according to the invention, measured at 20° C., is preferably in the range from 6.5 to 9.0, more preferably in the range from 7.0 to 8.6, especially in the range from 7.5 to 8.5.

The concentration of apoprotein B in the compositions according to the invention is preferably in the range from 0.0 g/l to 1.0 g/l, more preferably in the range from 0.01 g/l to 0.5 g/l, even more preferably in the range from 0.02 g/l to 0.3 g/l, especially in the range from 0.05 g/l to 0.2 g/l.

The lipoprotein concentration in the compositions according to the invention is preferably in the range from 0.0 mg/l to 1000.0 mg/l, more preferably in the range from 1.0 mg/l to 500.0 mg/l, even more preferably in the range from 5.0 mg/l to 250.0 mg/l, especially in the range from 50.0 mg/l to 125.0 mg/l.

In a particularly preferred version, the compositions according to the invention are used to speed up lung maturation of the fetus in order to further increase its chances of survival, more particularly in the case of premature birth. For this purpose, the concentration of at least one surfactant, preferably at least one phospholipid and/or at least one surfactant protein, more particularly at least one phospholipid, is increased in amniotic fluid. This can be achieved in particular by amnioinfusion of an aqueous composition having a higher concentration of the at least one surfactant than natural amniotic fluid.

In this connection, found to be particularly advantageous are compositions having a total lipid fraction of all phospholipids greater than 120.0 mg/l, preferably greater than 140.0 mg/l, more preferably greater than 160.0 mg/l, even more preferably greater than 175.0 mg/l, yet even more preferably greater than 200.0 mg/l, yet still even more preferably greater than 250.0 mg/l, especially greater than 400.0 mg/l.

The phosphatidylcholine concentration of preferred compositions is preferably greater than 120.0 mg/l, more preferably greater than 140.0 mg/l, even more preferably greater than 160.0 mg/l, yet even more preferably greater than 175.0 mg/l, yet still even more preferably greater than 200.0 mg/l, very preferably greater than 250.0 mg/l, especially greater than 400.0 mg/l.

The dipalmitoylphosphatidylcholine concentration of preferred compositions is preferably greater than 50.0 mg/l, more preferably greater than 60.0 mg/l, even more preferably greater than 75.0 mg/l, yet even more preferably greater than 100.0 mg/l, yet still even more preferably greater than 125.0 mg/l, very preferably greater than 150.0 mg/l, especially greater than 200.0 mg/l.

The palmitoylmyristolphosphatidylcholine concentration of preferred compositions is preferably greater than 7.0 mg/l, more preferably greater than 10.0 mg/l, even more preferably greater than 15.0 mg/l, yet even more preferably greater than 20.0 mg/l, yet still even more preferably greater than 25.0 mg/l, especially greater than 30.0 mg/l.

The phosphatidylglycerol concentration of preferred compositions is preferably greater than 12.0 mg/l, more preferably greater than 15.0 mg/l, even more preferably greater than 20.0 mg/l, yet even more preferably greater than 25.0 mg/l, yet still even more preferably greater than 30.0 mg/l, very preferably greater than 40.0 mg/l, especially greater than 50.0 mg/l.

The phosphatidylethanolamine concentration of preferred compositions is preferably greater than 6.0 mg/l, more preferably greater than 8.0 mg/l, even more preferably greater than 10.0 mg/l, yet even more preferably greater than 12.5 mg/l, yet still even more preferably greater than 15.0 mg/l, very preferably greater than 17.5 mg/l, especially greater than 20.0 mg/l.

The phosphatidylinositol concentration of preferred compositions is preferably greater than 6.0 mg/l, more preferably greater than 8.0 mg/l, even more preferably greater than 10.0 mg/l, yet even more preferably greater than 12.5 mg/l, yet still even more preferably greater than 15.0 mg/l, very preferably greater than 17.5 mg/l, especially at least 20.0 mg/l.

The phosphatidylserine concentration of preferred compositions is preferably greater than 1.5 mg/l, more preferably greater than 1.75 mg/l, even more preferably greater than 2.0 mg/l, yet even more preferably greater than 3.0 mg/l, yet still even more preferably greater than 4.0 mg/l, very preferably greater than 5.0 mg/l, especially greater than 6.0 mg/l.

The sphingomyelin concentration of preferred compositions is preferably greater than 10.0 mg/l, more preferably greater than 25.0 mg/l, even more preferably greater than 40.0 mg/l, yet even more preferably greater than 50.0 mg/l, yet still even more preferably greater than 60.0 mg/l, very preferably greater than 75.0 mg/l, especially greater than 400 mg/l.

The lysophospholipid concentration of preferred compositions is preferably greater than 0.6 mg/l, more preferably greater than 0.8 mg/l, even more preferably greater than 1.0 mg/l, yet even more preferably greater than 1.25 mg/l, yet still even more preferably greater than 1.5 mg/l, very preferably greater than 1.75 mg/l, especially greater than 2.0 mg/l.

The cholesterol concentration of preferred compositions is preferably greater than 6.0 mg/l, more preferably greater than 8.0 mg/l, even more preferably greater than 10.0 mg/l, yet even more preferably greater than 12.5 mg/l, yet still even more preferably greater than 15.0 mg/l, very preferably greater than 20.0 mg/l, especially at least 25.0 mg/l.

The concentration of surfactant protein A of preferred compositions is preferably greater than 6.0 mg/l, more preferably greater than 8.0 mg/l, even more preferably greater than 10.0 mg/l, yet even more preferably greater than 12.5 mg/l, yet still even more preferably greater than 15.0 mg/l, very preferably greater than 20.0 mg/l, especially greater than 25.0 mg/l.

The concentration of surfactant protein B of preferred compositions is preferably greater than 0.6 mg/l, more preferably greater than 0.8 mg/l, even more preferably greater than 1.0 mg/l, yet even more preferably greater than 1.25 mg/l, yet still even more preferably greater than 1.5 mg/l, very preferably greater than 2.0 mg/l, especially greater than 2.5 mg/l.

The concentration of surfactant protein D of preferred compositions is preferably greater than 12.0 mg/l, more preferably greater than 15.0 mg/l, even more preferably greater than 20.0 mg/l, yet even more preferably greater than 25.0 mg/l, yet still even more preferably greater than 30.0 mg/l, very preferably greater than 40.0 mg/l, especially greater than 50.0 mg/l.

The concentration of apoprotein B of preferred compositions is preferably greater than 0.15 mg/l, more preferably greater than 0.175 mg/l, even more preferably greater than 0.20 mg/l, yet even more preferably greater than 0.25 mg/l, yet still even more preferably greater than 0.30 mg/l, very preferably greater than 0.40 mg/l, especially greater than 0.55 mg/l.

The lipoprotein concentration of preferred compositions is preferably greater than 85.0 mg/l, more preferably greater than 90.0 mg/l, even more preferably greater than 100.0 mg/l, yet even more preferably greater than 125.0 mg/l, yet still even more preferably greater than 175.0 mg/l, very preferably greater than 250.0 mg/l, especially greater than 400.0 mg/l.

In addition, the compositions according to the invention contain water. The fraction thereof is preferably at least 50.0% by weight, more preferably at least 70.0% by weight, especially at least 90.0% by weight, based in each case on the total weight of the composition. In a particularly preferred version of the present invention, the compositions according to the invention do not contain any further solvent.

The fraction of components other than the essential and optional constituents explicitly mentioned in this application is preferably less than 5.0% by weight, more preferably less than 2.5% by weight, even more preferably less than 1.0% by weight, especially less than 0.5% by weight, based in each case on the total weight of the composition. In a particularly preferred version of the present invention, the compositions according to the invention consist exclusively of the essential and optional components explicitly mentioned in this application.

In the present invention, the compositions contain fewer than 70 amniotic cells per µl, preferably fewer than 50 per µl, more preferably fewer than 25 per µl, even more preferably fewer than 10 per µl, yet even more preferably fewer than 5.0 per µl, yet still even more preferably fewer than 1.0 per µl, especially none.

In addition, the compositions according to the invention contain by preference fewer than 750 fetal cells per µl, preferably fewer than 500 per µl, more preferably fewer than 250 per µl, even more preferably fewer than 100 per µl, yet even more preferably fewer than 50.0 per µl, yet still even more preferably fewer than 25.0 per µl, very preferably fewer than 10.0 per µl, very particularly preferably fewer than 1.0 per µl, especially none.

Furthermore, the compositions according to the invention contain preferably fewer than 70 trophoblast cells per µl, more preferably fewer than 50 per µl, even more preferably fewer than 25 per µl, yet even more preferably fewer than 10 per µl, yet still even more preferably fewer than 5.0 per µl, very preferably fewer than 1.0 per µl, especially none.

Moreover, the compositions according to the invention contain preferably fewer than 70 living cells per µl, more preferably fewer than 50 per µl, even more preferably fewer than 25 per µl, yet even more preferably fewer than 10 per µl, yet still even more preferably fewer than 5.0 per µl, very preferably fewer than 1.0 per µl, especially none.

In addition, the compositions according to the invention contain preferably fewer than 70 stem cells per µl, more preferably fewer than 50 per µl, even more preferably fewer than 25 per µl, yet even more preferably fewer than 10 per µl, yet still even more preferably fewer than 5.0 per µl, very preferably fewer than 1.0 per µl, especially none.

Additionally, the compositions according to the invention contain preferably fewer than 100 ng of cell-free fetal DNA per l, more preferably fewer than 50 ng per l, even more preferably fewer than 1 ng per l, yet even more preferably fewer than 500 pg per l, yet still even more preferably fewer than 100 pg per l, very preferably fewer than 30 pg per l, especially none.

In a very particularly preferred version of the present invention, the compositions do not comprise any human tissue remnants and preferably also do not comprise any animal tissue remnants, more particularly no infectious constituents and no human or animal DNA. Particularly preferably, they also do not contain any infectious animal constituents and animal DNA.

In addition, the compositions according to the invention are preferably sterile and preferably do not comprise any propagatable pathogens, more particularly no microorganisms or viruses. This can be achieved or ensured by customary sterilization methods.

Furthermore, the compositions according to the invention are preferably pyrogen-free. What are described as "pyrogenic" are those substances which have an inflammatory effect. These include in particular the substances which can produce fever in the event of parenteral administration, more particularly endotoxins from Gram-negative bacteria, constituents of Gram-positive bacteria, viral pyrogens, pyrogens as constituents of fungi, pyrogens of nonbiological origin.

The compositions according to the invention can be prepared in a manner known per se by mixing the components in the respective amounts to be used. Alternatively, it is also conceivable to dissolve in water a composition containing the desired components in the desired amount ratios, or to dilute an aqueous concentrate to the desired concentration.

Otherwise, care should be taken to prepare the aqueous compositions under extremely sterile conditions, so that the resulting compositions are virtually free of propagatable pathogens, more particularly microorganisms and viruses, even after prolonged storage, for example one year or longer.

The aqueous compositions according to the invention can be administered once, periodically or else continuously, and the advantages of the present invention can be observed in particular in the case of continuous administration.

Otherwise, the administration can be carried out in a manner known per se. In this connection, in order to avoid repetition, reference is made to the known amnioinfusion methods (with isotonic salt solution, more particularly with physiological saline solution), more particularly to the publications cited at the beginning.

For continuous amnioinfusion, it is recommended to use a port system, more particularly a subcutaneously implanted amniotic fluid replacement port system. Relevant port systems are described in the literature (Tchirikov M, Steetskamp J, Hohmann M, Koelbl H. Long-term amnioinfusion through a subcutaneously implanted amniotic fluid replacement port system for treatment of PPROM in humans. Eur J Obstet Gynecol Reprod Biol. 2010; 152: 30-33 and in WO2011154128), the disclosure of which is explicitly incorporated herein by reference.

In continuous amnioinfusion, the infusion rate is preferably greater than 1.0 ml/h, more preferably greater than 10.0 ml/h, even more preferably greater than 50.0 ml/h, especially greater than 75.0 ml/h. In addition, it is preferably less than 1000.0 ml/h, more preferably less than 500.0 ml/h, even more preferably less than 250 ml/h, especially less than 125.0 ml/h.

The duration of continuous amnioinfusion is in principle not subject to any particular restrictions. However, the advantages of the present invention come into effect especially in the case of long-term administration of the compositions according to the invention. Particularly advantageous is the procedure according to the invention for continuous amnioinfusions with a duration of at least 30 min, by preference at least 1 h, preferably at least 2 h, more preferably at least 4 h, even more preferably at least 12 h, yet even more preferably at least 24 h, yet still even more preferably at least 3 days, very preferably at least one week, very particularly preferably at least 3 weeks, especially at least 6 weeks. In this case, occasional interruptions to the continuous administration are possible. However, they should advantageously last not longer than 100% of the time, preferably not longer than 50% of the time, since the last interruption.

If the compositions according to the invention are not completely homogeneous and are, for example, present as aqueous suspensions or emulsions, they are prepared as freshly as possible, i.e., immediately just before their application. Accordingly, protection is likewise sought in the present invention for combinations comprising the individual components of the aqueous compositions according to the invention in at least two different fractions.

In a particularly preferred version of the present invention, the concentrations of the constituents of the compositions are changed over time during their preferably continuous administration in order to take into account the particular age of the fetus. For instance, the surfactant concentration, more particularly the phospholipid concentration, can be increased if necessary in order to speed up lung maturation. In addition, the concentration of one or more surfactant proteins can be increased in order to promote lung maturation.

According to the first aspect of the present invention, the composition can be advantageously used not just in amnioinfusion. Further application areas of said composition according to the invention comprise in particular all medical applications in which a preferably hypotonic aqueous composition containing phospholipids is used. Particularly preferred application areas include the rinsing of body cavities, preferably the rinsing out of purulent cavities, more particularly in the lungs, for example in the context of bronchoalveolar lavage, and also the rinsing of body regions covered with membranes, more particularly mucous membranes.

EXAMPLES

The present invention will now be further illustrated by means of examples and comparative examples, without hereby intending to limit the concept of the invention.

Examples 1, 2, 3 and 4

Table 1 shows examples of aqueous compositions for amnioinfusions, more particularly for continuous amnioinfusions, which are particularly suitable for the purposes of the present invention.

TABLE 1

Aqueous compositions for amnioinfusions

|  | Example 1 | Example 2 | Example 3 | Example 4 |
|---|---|---|---|---|
| Osmolarity [mosm/l] | 240-300 | 271 | 271 | 271 |
| Sodium [mmol/l] | 130-145 | 134.8 | 134.8 | 134.8 |
| Potassium [mmol/l] | 3.5-4.5 | 3.9 | 3.9 | 3.9 |
| Calcium [mmol/l] | 1-2.5 | 1.9 | 1.9 | 1.9 |
| Magnesium [mmol/l] | 0-2 | 0.57 | 0.57 | 0.57 |
| Chloride [mmol/l] | 100-120 | 109.5 | 109.5 | 109.5 |
| Urea [mg/dl] | 0-10 | 10 | 10 | 10 |
| Uric acid [mg/dl] | 0-5 | 3.5 | 3.5 | 3.5 |
| Phosphate [mg/dl] | 0-8 | 3.3 | 3.3 | 3.3 |
| Glucose [mg/dl] | 0-340 | <60.0 | <60.0 | <60.0 |
| Lactate [mmol/l] | 0-20 | 9.1 | 9.1 | 9.1 |
| Citrate [mg/l] | 0-100 | 66.5 | 66.5 | 66.5 |
| Hydrogencarbonate [mmol/l] | 5-100 | 16.9 | 16.9 | 16.9 |
| Total protein [g/l] | 0-10 | 3 | 3 | 3 |
| Albumin [g/dl] | 0-5 | <2 | <2 | <2 |
| Copper [µg/dl] | 0-150 | 16 | 16 | 16 |
| Selenium [µg/dl] | 0-50 | <13.3 | <13.3 | <13.3 |
| Zinc [µg/dl] | 0-30 | 10-24 | 10-24 | 10-24 |
| SURFACTANT fractions | | | | |
| Total lipids [mg/l] | 0-2000 | 100-339 | 100-339 | 500-1695 |
| Phosphatidylcholine (PC) [mg/l] (preferably 80% of total lipids) | 0-1000 | 93 | 93 | 465 |
| Dipalmitoylphosphatidylcholine [mg/l] (preferably 36%-60% of PC) | 0-600 | 47 | 47 | 235 |
| Palmitoylmyristol-phosphatidylcholine [mg/l] | 0-200 | 6.2 | 6.2 | 31 |
| Phosphatidylglycerol [mg/l] (preferably 12% of PC) | 0-200 | 11 | 11 | 55 |
| Phosphatidylethanolamine [mg/l] (preferably 5% of PC) | 0-100 | 4.5 | 4.5 | 22.5 |
| Phosphatidylinositol [mg/l] (preferably 4% of PC) | 0-70 | 4 | 4 | 20 |
| Phosphatidylserine [mg/l] (preferably 1.5% of PC) | 0-50 | 1.4 | 1.4 | 7 |
| Sphingomyelin [mg/l] (preferably 1% of PC) | 0-1000 | 1 | 10-40 | 50-100 |

TABLE 1-continued

Aqueous compositions for amnioinfusions

| | Example 1 | Example 2 | Example 3 | Example 4 |
|---|---|---|---|---|
| Lysophospholipid [mg/l] (preferably <1% of PC) | 0-10 | 0.5 | 0.5 | 2.5 |
| L/S ratio | >1.5 | >2.0 | >2.0 | >2.0 |
| Cholesterol [mg/l] (preferably 5%-10% of total lipids) | 0-100 | 5 | 5 | 25 |
| Surfactant protein A [mg/l] | 0-500 | 5.6 | 5.6 | 28 |
| Surfactant protein B [mg/l] | 0-100 | 0.54 | 0.54 | 2.7 |
| Surfactant protein D [µg/l] | 0-1000 | 11.8 | 11.8 | 59 |
| Apoprotein B g/l | 0-1 | 0.12 | 0.12 | 0.6 |
| Lipoprotein mg/l | 0-1000 | 84.53 | 84.53 | 422 |
| Water | The rest | The rest | The rest | The rest |
| pH | 7-8.6 | 8.35 | 8.35 | 8.35 |
| Amniotic cells [µl] | 0.0 | 0.0 | 0.0 | 0.0 |
| Fetal cells [µl] | 0.0 | 0.0 | 0.0 | 0.0 |
| Trophoplast cells [µl] | 0.0 | 0.0 | 0.0 | 0.0 |
| Living cells [µl] | 0.0 | 0.0 | 0.0 | 0.0 |
| Stem cells [µl] | 0.0 | 0.0 | 0.0 | 0.0 |
| Fetal DNA [pg/l] | 0.0 | 0.0 | 0.0 | 0.0 |
| Nonfetal DNA [pg/l] | <30 | <30 | <30 | <30 |

The glucose concentration in the examples according to the invention is preferably in the range from 0.0 mg/dl to 340.0 mg/dl. It is more preferably less than 300.0 mg/dl, even more preferably less than 200.0 mg/dl, yet even more preferably less than 100.0 mg/dl, especially less than 60.0 mg/dl. In a very particularly preferred embodiment of the present invention, the examples contain less than 50.0 mg/dl, preferably less than 25.0 mg/dl, more preferably less than 10.0 mg/dl, especially zero, glucose.

Comparative Example 1

After continuous amnioinfusion of 2000 ml of physiological saline solution/24 h via a port system in the case of PPROM, there was an incident; the healthy patient developed hypertension which needed to be acutely treated with strong i.v. medication. It is assumed that this phenomenon was caused by a rise in angiotensin II by the activation of the RAAS system of the fetus by the salt present in the NaCl solution. The mother was adversely affected through the placenta with the vasoactive substances of the fetus.

Comparative Example 2

In the case of continuous Sterofundin amnioinfusion of 2000 ml/24 h via a port system, the mother experienced distinctly increased diuresis. The fetus drinks the fluid, which is conveyed to the mother through the placenta and excreted via the kidneys of the woman. This significantly reduces the effect of the lavage in PPROM in the case of intrauterine administration of Sterofundin solution.

Example 5

Continuous amnioinfusion of 2000 ml of example 4/24 proceeded without any problems. The solution was tolerated very well and there were no complications. In this way, it was possible to distinctly prolong the pregnancy and thus to distinctly reduce the risk of premature birth. Damage to organs of the fetus, especially its skin, its eyes and its digestive organs, more particularly its kidneys, was not observed.

The invention claimed is:

1. An aqueous composition for application in a method for the surgical or therapeutic treatment of the human or animal body or in a diagnostic method performed on the human or animal body, the aqueous composition consisting essentially of:
   (a) water, sodium ions, potassium ions, calcium ions, chloride ions, and hydrogencarbonate ions; and
   (b) optionally at least one selected from the group consisting of magnesium ions, urea, uric acid, phosphate ions, glucose, lactate salts, citrate salts, copper ions, selenium ions, zinc ions, phospholipids, lipids, surfactant proteins, proteins, amniotic cells, and non-fetal DNA;
   wherein:
   the composition contains fewer than 70 amniotic cells per µl,
   an osmolarity of the composition is in the range from 240.0 mosm/l to less than 308.0 mosm/l,
   a lactate salt concentration in the composition ranges from 0.0 mmol/l to 20.0 mmol/l, and
   a chloride ion concentration in the composition is not more than 130.0 mmol/l.

2. The aqueous composition as claimed in claim 1, wherein the composition contains at least one phospholipid.

3. The aqueous composition as claimed in claim 1, wherein the composition contains at least one surfactant protein.

4. The composition as claimed in claim 1, wherein the composition contains at least one of (i) one or more phospholipids and (ii) one or more surfactant proteins.

5. The composition as claimed in claim 1, wherein the composition contains at least one phosphatidylcholine.

6. The composition as claimed in claim 5, wherein a weight fraction of phosphatidylcholine, based on all lipids, is greater than 50.0% by weight.

7. The composition as claimed in claim 1, wherein the composition contains sphingomyelin.

8. The composition as claimed in claim 7, wherein a weight ratio of phospholipids to sphingomyelin is greater than 1.5.

9. The composition as claimed in claim 3, wherein a weight fraction of all surfactant proteins, based on the total weight of the composition, is greater than 1.0 mg/l.

10. The composition as claimed in claim 2, wherein a weight fraction of all phospholipids, based on the total weight of the composition, is greater than 120.0 mg/l.

11. The composition as claimed in claim 1, wherein the osmolarity of the composition is in the range from 240.0 mosm/l to 300.0 mosm/l.

12. The composition as claimed in claim 11, wherein a calcium ion concentration in the composition is in the range from 1.0 mmol/l to 2.5 mmol.

13. A combination comprising the individual components of a composition as claimed in claim 1 in at least two different fractions.

14. The composition as claimed in claim 4, wherein the osmolarity of the composition is in the range from 240.0 mosm/l to 300.0 mosm/l.

15. The composition as claimed in claim 14, wherein a calcium ion concentration in the composition is in the range from 1.0 mmol/l to 2.5 mmol.

16. A combination comprising the individual components of a composition as claimed in claim 4 in at least two different fractions.

17. A method for performing amnioinfusion, the method comprising infusing the aqueous composition according to claim 1 into an amniotic cavity of a human or an animal patient.

18. A method for performing amnioinfusion, the method comprising: infusing the aqueous composition according to claim 1 into an amniotic cavity of a human or an animal patient to maintain a normal fluid volume in the amniotic cavity of the patient.

19. A method for performing amnioinfusion, the method comprising continuously infusing the aqueous composition according to claim 1 into an amniotic cavity of a human or an animal patient.

20. A method for performing amnioinfusion, the method comprising continuously infusing the aqueous composition according to claim 1 into an amniotic cavity of a human or an animal patient for a period of at least 30 minutes.

21. A method for performing amnioinfusion, the method comprising infusing the aqueous composition according to claim 1 into an amniotic cavity of a pregnant human or a pregnant animal patient to treat preterm premature rupture of membranes in the patient.

22. The method of claim 21, wherein the patient is a human patient between week 13 of pregnancy and week 40 of pregnancy.

23. A method for performing amnioinfusion, the method comprising infusing the aqueous composition according to claim 1 into an amniotic cavity of a pregnant human or a pregnant animal patient to expedite lung maturation of a fetus in the pregnant patient, wherein the aqueous composition further comprises at least one surfactant.

24. A method for treating a patient, the method comprising rinsing a body cavity or region of a human or an animal patient with the aqueous composition according to claim 1.

25. A method for performing amnioinfusion, the method comprising infusing the aqueous composition according to claim 4 into an amniotic cavity of a human or an animal patient.

26. A method for performing amnioinfusion, the method comprising infusing the aqueous composition according to claim 4 into an amniotic cavity of a human or an animal patient to maintain a normal fluid volume in the amniotic cavity of the patient.

27. A method for performing amnioinfusion, the method comprising continuously infusing the aqueous composition according to claim 4 into an amniotic cavity of a human or an animal patient.

28. A method for performing amnioinfusion, the method comprising continuously infusing the aqueous composition according to claim 4 into an amniotic cavity of a human or an animal patient for a period of at least 30 minutes.

29. A method for performing amnioinfusion, the method comprising infusing the aqueous composition according to claim 4 into an amniotic cavity of a pregnant human or a pregnant animal patient to treat preterm premature rupture of membranes in the patient.

30. The method of claim 29, wherein the patient is a human patient between week 13 of pregnancy and week 40 of pregnancy.

31. A method for performing amnioinfusion, the method comprising infusing the aqueous composition according to claim 4 into an amniotic cavity of a pregnant human or a pregnant animal patient to expedite lung maturation of a fetus in the pregnant patient, wherein the aqueous composition further comprises at least one surfactant.

32. A method for treating a patient, the method comprising rinsing a body cavity or region of a human or an animal patient with the aqueous composition according to claim 4.

33. The aqueous composition as claimed in claim 1, wherein the aqueous composition consists of:
   (a) water, sodium ions, potassium ions, calcium ions, chloride ions, and hydrogencarbonate ions; and
   (b) optionally at least one selected from the group consisting of magnesium ions, urea, uric acid, phosphate ions, glucose, lactate salts, citrate salts, copper ions, selenium ions, zinc ions, phospholipids, lipids, surfactant proteins, proteins, amniotic cells, and non-fetal DNA.

34. The aqueous composition as claimed in claim 1, wherein the aqueous composition contains one or more proteins selected from the group consisting of albumin, apoprotein B, lipoprotein, and combinations thereof.

35. The aqueous composition as claimed in claim 1, wherein the aqueous composition contains one or more surfactant proteins selected from the group consisting of surfactant protein A, surfactant protein B, surfactant protein D, and combinations thereof.

36. The aqueous composition as claimed in claim 1, wherein the aqueous composition contains one or more lipids selected from the group consisting of cholesterol, saturated fatty acids, unsaturated fatty acids, and combinations thereof.

37. The aqueous composition as claimed in claim 1, wherein the aqueous composition contains one or more phospholipids selected from the group consisting of phosphatidylcholine, dipalmitoylphosphatidylcholine, palmitoylmyristolphosphatidylcholine, phosphatidylglycerol, phosphatidylethanolamine, phosphatidylinositol, phosphatidylserine, sphingomyelin, lysophospholipid, and combinations thereof.

38. The aqueous composition as claimed in claim 1, wherein the composition is in the form of a single fraction including the components of the composition.

39. The aqueous composition as claimed in claim 1, wherein:
   the osmolarity of the composition is in the range from 240.0 mosm/l to 280.0 mosm/l,
   the chloride ion concentration in the composition is in the range from 105.0 mmol/l to 115.0 mmol/l,
   a sodium ion concentration in the composition is less than 150.0 mmol/l,
   a potassium ion concentration in the composition is in the range from 3.5 mmol/l to 4.5 mmol/l,
   a calcium ion concentration in the composition is in the range from 1.5 mmol/l to less than 2.3 mmol/l,
   a magnesium ion concentration in the composition is in the range from 0.1 mmol/l to less than 0.8 mmol/l,
   a phosphate ion concentration in the composition is in the range from 0.1 mg/dl to 7.0 mg/dl, a citrate salt concentration in the composition is in the range from 0.0 mg/l to 100.0 mg/l,
a hydrogencarbonate ion concentration in the composition is in the range from 10.0 mmol/l to 20.0 mmol/l,
a copper ion concentration in the composition is in the range from 5.0 µg/dl to 50.0 µg/dl,
a zinc ion concentration in the composition is in the range from 5.0 µg/dl to 25.0 µg/dl, and
a pH of the composition is in the range from 7.5 to 8.5.

* * * * *